United States Patent [19]

Charm

[11] Patent Number: 4,754,656

[45] Date of Patent: Jul. 5, 1988

[54] SANITARY MILK SAMPLING APPARATUS AND METHOD

[76] Inventor: Stanley E. Charm, 21 Concolor Ave., Newton, Mass. 02158

[21] Appl. No.: 34,769

[22] Filed: Apr. 6, 1987

[51] Int. Cl.$^4$ .............................................. G01N 1/12
[52] U.S. Cl. ................................ 73/864.63; 73/864.91
[58] Field of Search ................ 73/864, 864.51, 864.91, 73/864.63; 220/263, 265, 318, 339, 96, 94 R; 206/569, 223, 602, 621, 634; 422/74; 141/110; 232/41 K, 41 A, 41 D

[56] References Cited

U.S. PATENT DOCUMENTS

| | | | |
|---|---|---|---|
| 2,624,201 | 1/1953 | Thomson | 73/864.51 |
| 2,668,448 | 2/1954 | Spencer | 73/864.63 |
| 3,960,021 | 6/1976 | Jones | 73/864.51 |
| 4,228,835 | 10/1980 | Robinson et al. | 206/628 |
| 4,262,802 | 4/1981 | Laauwe | 220/339 |
| 4,273,246 | 6/1981 | Thompson | 29/450 |
| 4,643,326 | 2/1987 | Klingler | 220/318 |

Primary Examiner—Stewart J. Levy
Assistant Examiner—Robert R. Raevis
Attorney, Agent, or Firm—Richard P. Crowley

[57] ABSTRACT

An integral, sanitary, plastic molded milk sampling apparatus, which apparatus comprises an elongated handle, a sampling vial and hinged cap to seal the sampling vial and a handle break-away means secured at the one end of the handle and at the other end to the cap or vial, so as to permit the apparatus to be used to obtain a sample of milk and thereafter, the handle broken away so as to permit the use of the sealing cap to seal the vial containing the milk sample.

14 Claims, 2 Drawing Sheets

SANITARY MILK SAMPLING APPARATUS AND METHOD

BACKGROUND OF THE INVENTION

Generally, milk is collected from a dairy farm by a milk tank truck driver whose duty includes the collection of milk samples from the co-op or farm and the identification of the sample so collected for possible future use. After the delivery of the milk by the milk tank truck driver to the milk processing plant, the milk collected is subject to various tests, particularly for beta lactam durgs, such as penicillin, or for microscopic examination for bacteria, dirt or other contamination prior to being processed. Where a milk tank truck is deemed to be contaminated, then further tests are generally conducted on the particular samples collected from the farms by the tank truck driver in order to determine the particular source farm of contamination.

It is the present practice for the farm to maintain a liquid sanitizing soultion, typically a chlorine-containing solution, near the milk collection point, and for the milk tank truck driver to employ a stainless steel ladle to sample the milk and to pour sampled milk into a plastic cylindrical vial, and then to seal the sampled milk with a sealing cap which conforms to milk sealing regulations. Prior to use of the milk sampling ladle, the sampling ladle is required to be immersed in the liquid sanitizing solution, and then rinsed in water to remove the sanitizing solution prior to use. Liquid sanitizing solutions, while subject to state inspection to be maintained at desired sanitizing levels, may be contaminated and may fail to maintain such sanitizing levels at all times. Further and importantly, while the tank truck driver or sampler is supposed to rinse the ladle after sampling, this may not be done at times, therefore leading to contamination of the milk to be sampled with the sanitizing solution.

It is therefore desirable to provide a new and improved sanitary milk sampling apparatus, method and technique which avoids the disadvantages and difficulties associated with the current state of the art milk sampling and which also provides additional benefits in cost and efficiency in the obtaining of effective and sanitary milk and other liquid samples.

SUMMARY OF THE INVENTION

The present invention relates to a sanitary, integral liquid particularly milk, sampling apparatus and method. In particular, the present invention concerns a plastic milk sampling ladle-type apparatus and method which employs a break-away handle with a sealing cap and sample container.

A sanitary liquid, particularly milk, sampling apparatus has been discovered, which apparatus comprises in combination an elongated handle element and a sampling container and sealing cap means for the container which provides for collection of a liquid sample, and which apparatus includes a handle breaking away arrangement and means in which one end of the handle is secured to the container and cap sealing means and which is subject to having the handle easily removed, or broken away, after sampling of the liquid and the handle then discarded, and the liquid so sampled sealed in the container.

The present apparatus and method provide significant and material advantages over the current practices regarding the sampling of milk and obviates the necessity for the use of liquid sanitizing compositions and mixtures or the use of a separate sampling ladle and separate sampling containers, thus avoiding the difficulties associated with their prior use as set forth in the Background of the Invention.

In particular, the present sanitary milk sampling apparatus and method may be composed of an unitary, integrally molded, all plastic or polymeric apparatus in which the break-away handle section, sampling container and sealing cap means are all contained and provided in a single molding operation. Further, the present apparatus provides for a relatively inexpensive sampling technique in a sanitary apparatus, since the molding of the milk sampling apparatus may be accomplished at high molding temperatures to provide sanitation or may be otherwise sanitized prior to packaging so that a liquid sampling composition mixture need not be employed or be maintained. Typically, the milk sampling apparatus may be sanitized and then packaged in thin film plastic, sanitary-type package which is easily removed prior to use or may be sanitized after packaging by irradiation.

The method of the present invention thereby involves sampling a liquid, such as milk, by obtaining a sample from a liquid source employing an elongated handle to which handle is secured in a break-away or removable manner the sampling container and optionally a sealing cap hingedly connected to the sample container, and thereafter breaking away the elongated handle after the sample has been obtained, sealing the sample liquid in the container with the sealing cap and thereafter discarding the broken away handle, thus obviating the need for separate sanitizing mixtures and the separate ladle and the sanitizing from time to time of the ladle.

In one embodiment of the invention, the elongated handle contains a break-away section secured to one end of the handle and formed or shaped or so mechanically weakened so that the handle may be easily removed by turning, twisting or bending the handle relative to the container or sealing cap. For example, an all plastic, molded milk sampling apparatus may have the break-away section containing a tapering or smaller diameter plastic section securing the one end of the handle to the outer edge of a sealing cap where the cap is attached to a container, or if desired, directly to the sealable container. The one end of the handle containing the break-away section may be secured directly to the container for the liquid and the sealing cap means separately supplied, or the one end of the handle may be secured to the sealable container containing a sealing cap secured thereto. More preferably, as illustrated and described, the one end of the handle containing a smaller diameter break-away section is secured to the outer edge of a sealable, flat-type, pressure fitting cap which is hingedly connected by a flat, semiflexible plastic strip about 180° from the handle connection to the vial so that the sanitary milk sampling apparatus may be formed in a single plastic molding operation. The apparatus should be sufficiently mechanically strong and structurally stable to permit the use of the apparatus to secure the liquid sample in the container prior to removing the handle.

While the milk sampling apparatus and method is particularly adapted to overcome the disadvantages and to provide advantages in the sampling of milk, it is recognized that the liquid sampling apparatus may be employed in the collection of samples of a wide variety of liquid materials where all or some of the present disadvantages and difficulties associated with milk sampling are also present.

The invention will be described for the purposes of illustration only in connection with a particular illustrated embodiment; however, it is recognized that those persons skilled in the art may make various changes, modifications, additions and improvements in the illustrated embodiment, all falling within the spirit and scope of the invention.

DESCRIPTION OF THE EMBODIMENTS

Figure 1:
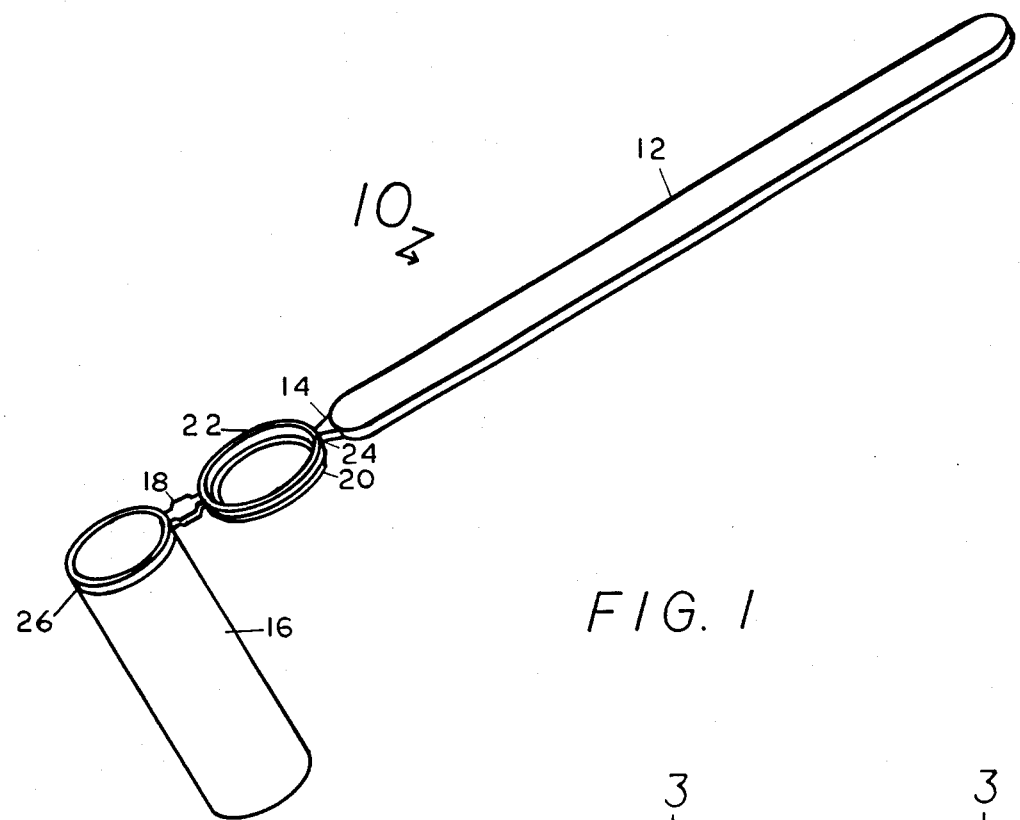
FIG. 1 is a perspective view from above of a milk sampling apparatus of the invention.
Figure 2:
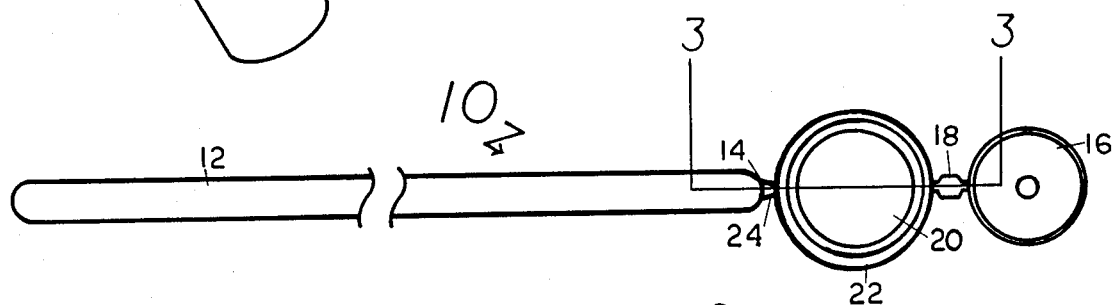
FIG. 2 is a top plan view of the milk sampling apparatus of FIG. 1.
Figure 3:
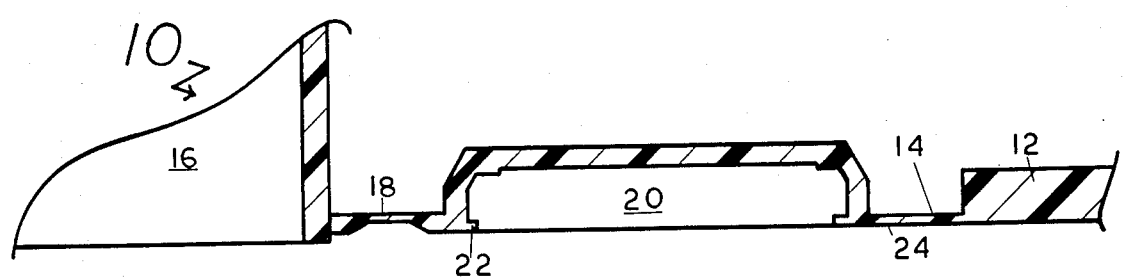
FIG. 3 is an enlarged fragmentary sectional view along line 3—3 of the milk sampling apparatus of FIG. 2.

With reference to FIGS. 1–3, there is shown an unitary, plastic molded milk sampling apparatus 10 comprising an elongated rectangular handle 12 which at the one end thereof contains a plastic, tapering, flat, break-away section 14 of diminished thickness and mechanical strength than the handle 12 and a transparent container 16 of approximately 50 ml to 100 ml integrally secured by a thin, flat cap hinge section 18 to a plastic sealing cap 20, which container has an external, peripheral, ridge 26 thereon to provide a sealing stop for the edge of the cap 20 in the sealed condition. The break-away section 14 comprises a flat, tapered, diminished section so that upon hand twisting, turning or bending of the handle 12 by the user, this section will break away at its narrow end directly adjacent the edge of the sealable cap 20. There is a slight peripheral ridge 22 on the internal periphery of the cap 20 so as to provide an effective seal for the milk sample taken when the cap 20 is hand-pressed over the open top of the container 16 into a closed position.

Figure 4:
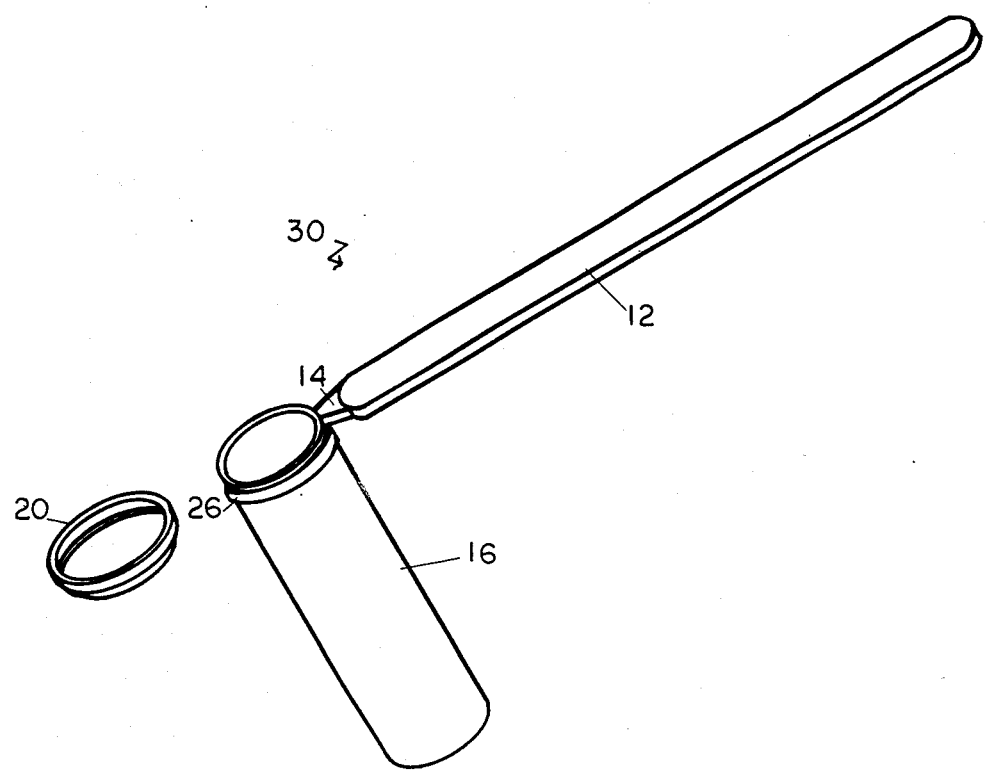
FIG. 4 is an alternate embodiment of the milk sampling apparatus.

FIG. 4 is an alternate embodiment of the milk sampling apparatus of the invention wherein the apparatus 30 has the tapering, plastic, break-away section 14 at the one end of the handle 12 secured directly to the edge of the sample container 16 with the sealing cap 20 not connected to the container 16, but separately supplied as shown. In use, a sample of milk is obtained in container 16, the handle 12 broken off and the sealing cap 20 used to seal the container 16.

The milk sampling apparatus 10 as illustrated and described may be hot molded of polyethylene or polypropylene. The break-away section 14 may be approximately one-eighth of an inch in length and tapered and having thickness of about 0.015 inches. In use, the apparatus 10 may be removed from a transparent film package (not shown), the container 16 dipped in the milk to be sampled, the handle 12 broken off easily from the cap 20 at 14, and the cap 20 sealed by ridges 22 and 26 on the container 16.

The milk sampling apparatus as described and illustrated thus provides an easy, simple, sanitized method for sampling milk.

What is claimed is:

1. A platic, sanitary, liquid sampling apparatus which comprises:

(a) an elongated handle having a one and an other end;
(b) a liquid sample container;
(c) a cap means to seal a liquid sample in the container; and
(d) handle break-away means secured by a hand break-away portion at the one end of the handle to the container or to the cap means which cap means is secured to the container so as to permit the use of the handle in obtaining a liquid sample from a liquid source and to provide after so sampling the material destruction and breaking away of the break-away portion of the handle as the one end.

2. The apparatus of claim 1 wherein the handle break-away means is secured to the one end of the handle element and to the peripheral edge of the cap means, and the cap is hingedly secured to the sample container.

3. The apparatus of claim 1 wherein the sample container comprises a cylindrical sample container having a one open end, and the cap means comprises a sealing cap to be sealed over the said ridge and about the open end of the cylindrical sample container.

4. The apparatus of claim 1 wherein the sample container and cap means comprises a cylindrical sample container having one open end and a plastic hinge means to connect the cylindrical sample container to the cap means, and the said handle break-away means is secured to the edge of the cap means about 180° from the said hinge means.

5. The apparatus of claim 1 wherein the break-away means comprises a material secured to the one end of the handle and of less thickness than the handle and subject to mechanical breaking when the handle is hand twisted, turned or bent.

6. The apparatus of claim 1 wherein the break-away means comprises a tapered plastic material.

7. The apparatus of claim 1 wherein the apparatus is composed of a molded polyethylene or polypropylene plastic material.

8. The apparatus of claim 1 wherein the one end of the handle is secured via the handle break-away means directly to the exterior of the container.

9. A sanitary, integral molded, plastic milk sampling apparatus which comprises in combination:

(a) an elongated, disposable handle having a one end and an other end;
(b) a milk sample container having a one open end;
(c) a cap means to seal a sample of milk in said sample container, the cap means having a peripheral edge;
(d) a hinge means to connect the cap means to the milk sample container and adjacent the said open end; and
(e) a handle break-away means to secure the one end of the disposable handle to the peripheral edge of the cap means, the handle break-away means generally axially aligned with the longitudinal axis of the hinge means and composed of a short section of reduced dimensions and thickness than the one end of the handle so as to permit the use of the handle to obtain a sample of the milk in the sample container and to provide, after the milk sampling, the sealing of the sample container with the cap means and the breaking away of the handle at said section.

10. A method of securing a sample of milk from a milk source under sanitary conditions which method comprises:

(a) obtaining a sample of milk from a milk source by use of a plastic milk sampling apparatus which comprise a sealing cap and a sample container, the sample container or the sealing cap with the container integrally secured thereto, secured by a hand breakable portion to the one end of an elongated handle;

(b) sealing the milk sample in the sample container with the sealing cap; and (c) breaking away the one end of the handle from the sample container or sealing cap after the milk sample has been obtained by the material breaking of the hand breakable portion to permit discarding of the break-away handle.

11. The method of claim 10 wherein said sealing cap is hingedly connected to the said sample container and which method includes sealing the milk sample in the sample container by the use of the hingedly connected sealing cap.

12. The method of claim 10 which includes securing the handle in a break-away manner to the peripheral edge of the sealing cap, which sealing cap is hingedly connected to the sample container.

13. The method of claim 10 wherein the milk sampling apparatus is a unitary, sanitary, molded, plastic apparatus comprising polyethylene or polypropylene.

14. The method of claim 10 wherein the sealing cap has an external, peripheral edge which fits over the end of the sample container and the sample container having a one open end an external, peripheral ridge adjacent the open end and which includes sealing the sealing cap to the sample container by snap fitting the sealing cap edge over the ridge of the sample container.

* * * * *

UNITED STATES PATENT AND TRADEMARK OFFICE
CERTIFICATE OF CORRECTION

PATENT NO. : 4,754,656

DATED : July 5, 1988

INVENTOR(S) : Stanley E. Charm

It is certified that error appears in the above-identified patent and that said Letters Patent is hereby corrected as shown below:

In column 3, claim 1, line 67, delete "platic" and insert --plastic--.

In column 4, claim 3, line 20, after "end" delete "," and insert --and a peripheral ridge adjacent the open end,--.

Signed and Sealed this

Twenty-second Day of November, 1988

Attest:

DONALD J. QUIGG

Attesting Officer

Commissioner of Patents and Trademarks